United States Patent [19]

Meessen et al.

[11] Patent Number: 4,801,745
[45] Date of Patent: Jan. 31, 1989

[54] IMPROVED PROCESS FOR THE PREPARATION OF UREA

[75] Inventors: Jozef H. Meessen, Wijlre; Rudolf Sipkema, Geleen, both of Netherlands

[73] Assignee: Stamicarbon B.V., Geleen, Netherlands

[21] Appl. No.: 895,430

[22] Filed: Aug. 11, 1986

[30] Foreign Application Priority Data

Aug. 12, 1985 [NL] Netherlands ................. 8502227

[51] Int. Cl.$^4$ .................. C07C 126/00; C07C 126.02
[52] U.S. Cl. ........................ 564/70; 564/71; 564/72; 564/67
[58] Field of Search ............. 564/70, 72, 71, 67

[56] References Cited

U.S. PATENT DOCUMENTS 3,406,201 10/1968 Baumann et al. ............... 564/70
3,936,500  2/1976 Kaasenbrood et al. .......... 564/70
4,138,434  2/1979 Lagana et al. ............... 564/70 X
4,314,077  2/1982 Zardi et al. ................ 564/70
4,354,040 10/1982 Inoue et al. ................ 564/70 X

FOREIGN PATENT DOCUMENTS 190290 7/1961 U.S.S.R. ..................... 564/70

OTHER PUBLICATIONS

Kirk-Othmer, "Encyclopedia of Chemical Technology", vol. 21, pp. 37 to 51 (1970).

Primary Examiner—Floyd D. Higel
Attorney, Agent, or Firm—Cushman, Darby & Cushman

[57] ABSTRACT

Process for the preparation of urea in which a urea synthesis solution containing carbamate and free ammonia is formed in a high-pressure part in a synthesis zone at an $NH_3/CO_2$ molar ratio of up to 4:1, a temperature of at least 175° C. and the corresponding pressure, a portion of the carbamate is decomposed in a first decomposition stage at synthesis pressure or lower pressure by a stripping treatment with carbon dioxide while heating is applied, and the gas mixture thus obtained is at least in part condensed and the condensate and the non-condensed portion of the gas mixture, if any, are returned to the synthesis zone, in at least two further decomposition stages a further portion of the carbamate still present is decomposed and the gas mixture formed is separated, in the first of the further decomposition stages a pressure of 12–30 bar being maintained and heat being supplied, and the remaining urea-containing solution is processed further by evaporation to a concentrated urea solution and, if desired, solid urea.

The gas mixture, formed on expansion of the stripped urea synthesis solution to a pressure equal to or higher than the pressure in the first one of the further decomposition stages, is brought into direct contact in a contact zone with the solution remaining after further amounts of carbamate still present have herein been decomposed and the gases thus formed have been separated. The remaining gas mixture is thereafter discharged from the contact zone and is condensed. The condensate is returned to the high-pressure part of the urea synthesis.

4 Claims, 1 Drawing Sheet

U.S. Patent
Jan. 31, 1989
4,801,745
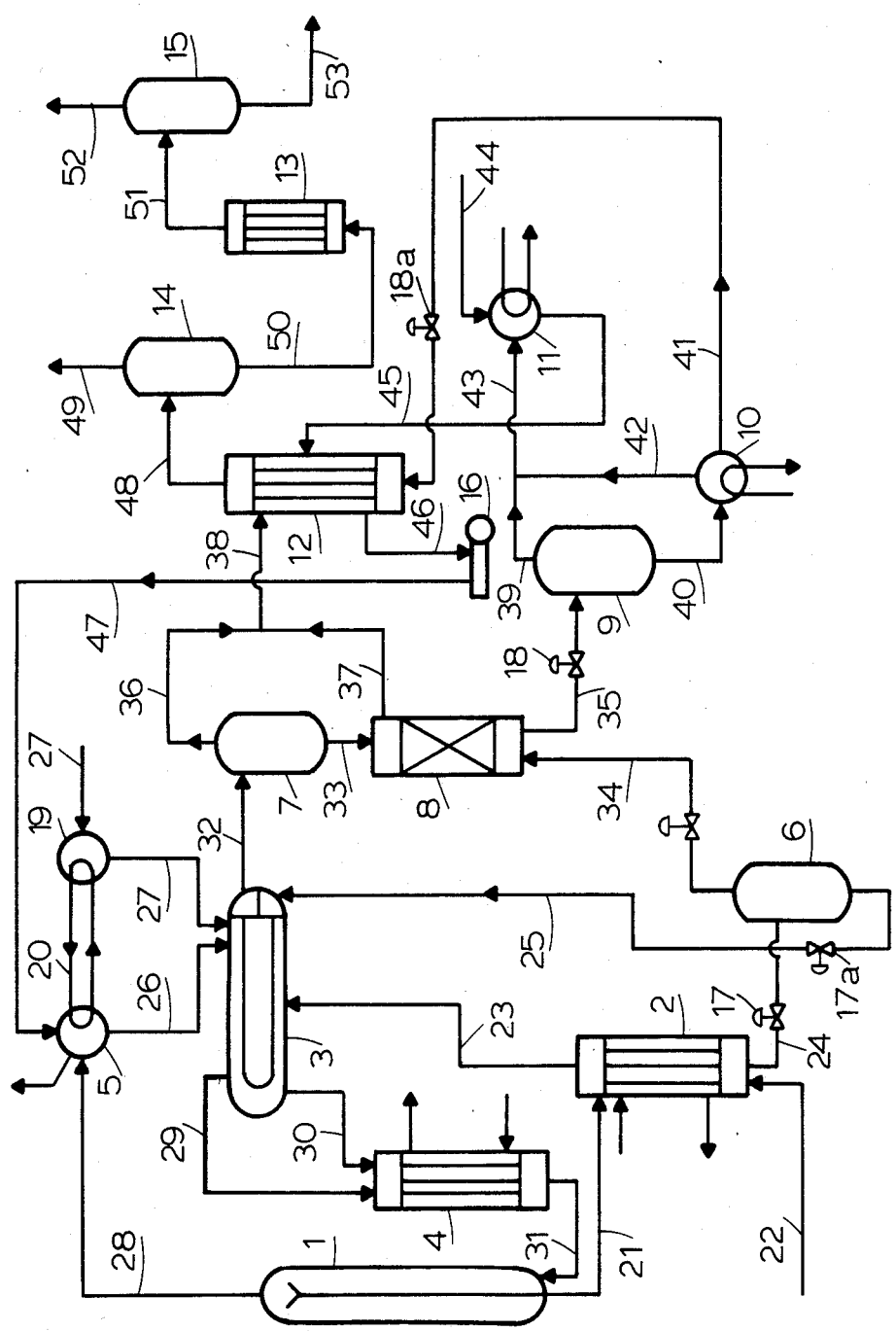

IMPROVED PROCESS FOR THE PREPARATION OF UREA

The invention relates to a process for the preparation of urea from ammonia and carbon dioxide.

When ammonia and carbon dioxide at a suitable pressure (for instance 125–350 atm) and at a suitable temperature (for instance 170°–250° C.) are introduced into a synthesis zone, first ammonium carbamate is formed according to the reaction:

$$2 NH_3 + CO_2 \rightarrow H_2N-CO-ONH_4$$

From the ammonium carbamate formed, urea is subsequently formed through dehydration according to the reversible reaction:

$$H_2N-CO-ONH_4 \rightleftharpoons H_2N-CO-NH_2 + H_2O$$

The degree to which the conversion to urea takes place depend, inter alia, on the temperature and the ammonia excess used. As reaction product, a solution is obtained that consists mainly of urea, water, ammonium carbamate and free ammonia. The ammonium carbamate and the ammonia are to be removed from the solution; mostly, they are returned to the synthesis zone. This synthesis zone may consist of separate zones for carbamate and urea formation, but these zones may also be accommodated in one apparatus.

One process for the preparation of urea that has found wide use in practical applications is described in European Chemical News, Urea Supplement of Jan. 17, 1969, pages 17–20. In said process, the urea synthesis solution formed at high temperature and pressure in the synthesis zone is subjected to a stripping treatment at synthesis pressure by countercurrently contacting the solution with gaseous carbon dioxide while supplying heat, so that the larger part of the carbamate present in the solution decomposes into ammonia and carbon dioxide, and these decomposition products are in gaseous form expelled from the solution and discharged together with a minor amount of water vapour and the carbon dioxide used for stripping. The heat required for the stripping treatment is obtained by condensation of high-pressure steam of 15–25 bar on the shell side of the tubes of the vertical heat exchanger in which stripping takes place.

The gas mixture obtained in the stripping treatment passes to a first condensation zone and is for the larger part condensed and absorbed in an aqueous solution originating from the further treatment of the urea-containing solution, upon which both the aqueous carbamate solution thus formed and the non-condensed gas mixture are sent to the synthesis zone for urea formation. Here, the heat required for the conversion of carbamate into urea is obtained by further condensation of the gas mixture.

The stripped urea synthesis solution is subsequently expanded to a low pressure of, for instance, 3–6 bar and heated by means of steam so as to remove the ammonia and carbon dioxide still partly present as carbamate from the stripped urea solution. The gas mixture obtained in these operations, which also contains water vapour, is condensed and absorbed in an aqueous solution in a second condensation zone, which is operated at low pressure, and the resulting dilute carbamate solution is returned to the high pressure section of the urea synthesis and eventually introduced into the synthesis zone. The remaining urea-containing solution is reduced further in pressure and is worked up to a urea solution or melt that may be processed to solid urea. To this end, the aqueous urea solution is usually evaporated in two evaporation stages and the urea melt thus obtained is processed to granules, or the urea solution is crystallized. The gases obtained during evaporation or crystallization, which besides water vapour contain, inter alia, ammonia, carbon dioxide and entrained fine urea droplets, are condensed, yielding so-called process condensate. A portion of the process condensate is used as absorption agent for the gas mixture in the second condensation zone. The remainder can be treated with high-pressure steam for decomposition into ammonia and carbon dioxide of urea contained in it and recovery of these decomposition products together with the ammonia and carbon dioxide already present as such.

It has already been proposed to incorporate an additional decomposition stage in such a process in which further amounts of carbamate, that are still present in the stripped urea synthesis solution, are decomposed at a pressure of 12–25 kg/cm$^2$ (see U.S. Pat. No. 4,354,040). A drawback of such an additional decomposition stage is that the molar ratio of the ammonia and carbon dioxide not converted into urea in the urea-containing solution discharged from this additional decomposition stage is relatively high. As a consequence, this ratio will also be relatively high in the gas mixture formed on decomposition of carbamate still present in the second of the further decomposition stages. For complete condensation into a crystal-free carbamate solution of such gas mixtures, considerable amounts of water or water-containing absorbents are required, which are ultimately returned to the synthesis zone, and adversely affect the conversion of ammonia and carbon dioxide into urea. If, as is done in the process described, a portion of the carbon dioxide required in the synthesis is supplied to the last decomposition stage, an NH$_3$/CO$_2$ molar ratio that is more favourable for complete condensation under the prevailing conditions is achieved in the gas mixture obtained in this stage. In this condensation, however, the heat of condensation is released at the low temperature level belonging to this decomposition stage, as a result of which the heat released can hardly be put to any efficient use and must be discharged by means of cooling water.

The object of the invention is to provide a process for the preparation of urea which avoids the above-mentioned drawback. According to the invention this is achieved if the gas mixture and the remaining solution, which is obtained on expansion of the stripped urea synthesis solution, are subjected to a special treatment. As a result of the stripping treatment with carbon dioxide, the stripped urea synthesis solution contains relatively much carbon dioxide. The gas mixture obtained on expansion of this solution therefore also contains relatively much carbon dioxide. When this gas mixture is contacted with the remaining solution, after further amounts of carbamate still present in it have been decomposed and the gases thus formed have been separated, the NH$_3$/CO$_2$ molar ratio is reduced substantially in the solution and increased in the gas mixture. As a result of this treatment, also in the subsequent decomposition stage a gas mixture is obtained which, without further correction measures, such as addition of extra carbon dioxide, and without addition of excessively large amounts of water, can be condensed at a relatively high temperature allowing efficient use of the heat of condensation.

The invention therefore relates to a process for the preparation of urea in which:

a urea synthesis solution containing carbamate and free ammonia is formed in a high-pressure part in a synthesis zone at an $NH_3/CO_2$ molar ratio of up to 4:1, a temperature of at least 275° C. and the corresponding pressure, a portion of the carbamate is decomposed in a first decomposition stage at synthesis pressure or lower pressure by a stripping treatment with carbon dioxide while heating is applied, and the gas mixture thus obtained is at least in part condensed and the condensate and the non-condensed portion of the gas mixture, if any, are returned to the synthesis zone, in at least two further decomposition stages a further portion of the carbamate still present is decomposed and the gas mixture formed is separated, in the first of the further decomposition stages a pressure of 12-30 bar being maintained and heat being supplied, and the remaining urea-containing solution is processed further by evaporation to a concentrated urea solution and, if desired, solid urea.

This process is characterized in that the gas mixture, formed on expansion of the stripped urea synthesis solution to a pressure equal to or higher than the pressure in the first one of the further decomposition stages, is brought into direct contact in a contact zone with the solution remaining after further amounts of carbamate still present in it have been decomposed and the gases thus formed have been separated, following which the remaining gas mixture is discharged from the contact zone and condensed and the condensate is returned to the high-pressure part of the urea synthesis.

Decomposition of the further amounts of carbamate still present in the expanded stripped urea synthesis solution may be effected by heating of the solution. Preferably, the further amounts of carbamate still present in the expanded stripped urea synthesis solution are decomposed by passing this solution in indirect heat exchange with the condensing gas mixture in a first condensation zone. If the conditions in the first condensation zone are chosen such that also a considerable amount of urea, for instance at least 30% of the equilibrium amount that can be achieved under the reaction conditions, is formed from the carbamate formed on condensation, then the heat is released at such a temperature level that a considerable portion of the carbamate still present in the stripped urea synthesis solution is decomposed into ammonia and carbon dioxide. As a rule, a surplus of heat will even be available. This heat may then be discharged in a second high-pressure condensation zone by means of boiler feed water, which is thereby converted into low-pressure steam of 4-9 bar. The amount of gas mixture to be condensed and the amount to be fed to the synthesis zone can be controlled by means of the steam pressure in this second high-pressure condensation zone. This offers the possibility of controlling the temperature in the synthesis zone within certain limits. The gas mixture formed on carbamate decomposition as a result of the heat exchange with the condensing gas mixture in the first condensation, is separated from the remaining solution, before according to the invention this solution is brought into direct contact with the gas mixture obtained on expansion to a pressure of 12-30 bar of the stripped urea synthesis solution. The solution obtained in the first of the further decomposition stages has a relatively high $NH_3/CO_2$ molar ratio, which is higher than the $NH_3/CO_2$ ratio of the stripped urea synthesis solution. If this solution is contacted with the carbon dioxide rich gas mixture that is formed on expansion of the stripped urea synthesis solution, the $NH_3/CO_2$ molar ratio of the solution is decreased to such a value that also the gas mixture obtained on decomposition of carbamate in the further decomposition stages can be condensed without supply of excessive amounts of water. The gas mixture formed on indirect heat exchange in the first condensation zone and the gas mixture remaining in the first condensation zone and the gas mixture remaining after the direct contact can be combined and condensed. Condensation preferably is effected using the carbamate solution obtained on further processing of the stripped urea synthesis solution in a decomposition stage operated at a pressure of, for instance, 1-10 bar, which carbamate solution is then first brought up to the prevailing pressure in the 12-30 bar pressure range by means of a pump. The heat of condensation can then be obtained at a level of 145°-110° C., which is appreciably higher than in the process according to the above-mentioned U.S. Pat. No. 4,354,040. The heat released on condensation can, for instance, be utilized by heat exchange with the urea solution to be evaporated. If this urea solution to be evaporated is passed countercurrent to the condensing gas mixture and the carbamate solution is supplied at a point between the supply of the urea solution to be evaporated and the supply of the gas mixture to be condensed, the urea solution can be concentrated, for instance, at temperatures between 85° and 130° C. from about 70 wt. % to about 95 wt. %. These values largely correspond with the concentration normally achieved in the first evaporation stage in the process known from European Chemical News that was discussed above.

Compared with this known process, the process according to the invention has the advantage that no excessively large amounts of water are needed for condensation of the gas mixtures obtained in the several decomposition stages, which has a favourable effect on the synthesis efficiency. Since no carbon dioxide is fed to the low-pressure stage, the total amount of carbon dioxide required in the synthesis can be used for the stripping treatment while the heat of condensation of this carbon dioxide can also be utilized efficiently for heating of the stripped urea synthesis solution and steam formation. For decomposition of the further amounts of carbamate and expulsion of the gas mixtures thus formed in the decomposition stage operated at 12-30 bar, no additional amount of high-pressure steam is required, as in the known process, but use is made of the heat content of the gas mixture obtained in the stripping treatment for this carbamate decomposition. In addition, the heat content of the gas mixture from the decomposition stage operated at 12-30 bar can suitably be used in concentrating the urea solution obtained to an approx. 95 wt. % solution by evaporation.

The invention will be elucidated with reference to the FIGURE and the example, without however being limited thereto.

In the FIGURE a synthesis zone is represented by 1, a stripping zone by 2, a first and a second high-pressure condensation zone by 3 and 4, respectively, and a scrubbing zone by 5. 6, 7 and 9 are devices for separating liquids and gases. A zone for contacting liquids and gases is represented by 8. 10 stands for a heat exchanger and 11 for a carbamate condensation zone operated at low pressure. The heating zones of the first and the second concentration stage are represented by 12 and 13, respectively, the associated devices for separation of the water vapour formed in concentrating by 14 and 15, respectively. A carbamate pump is indicated by 16; 17, 17a, 18 and 18a are expansion valves.

The urea synthesis solution formed in urea synthesis zone 1 at a pressure of 125–250 bar, a temperature of 175°–220° C. and an $NH_3/CO_2$ molar ratio of 2.7–4.0, for instance at 140 bar, 183° C. and an $NH_3/CO_2$ molar ratio of 3.2, which contains free ammonia and non-converted ammonium carbamate besides urea and water, is fed to stripping zone 2 via 21. Countercurrent to the urea synthesis solution, via 22 carbon dioxide, which has been compressed to synthesis pressure in a compression device not shown and to which passivation air may, if desired, have been added, is passed to this stripping zone. Stripping zone 2 preferably is designed as a vertical shell-and-tube heat exchanger. The heat required in the stripping treatment is obtained by condensation of high-pressure steam of, for instance, 14–40 bar in the shell side of the heat exchanger. The expelled gas mixture, which contains equilibrium amounts of water vapour besides ammonia and carbon dioxide, and the carbon dioxide required for the stripping treatment are passed through 23 into first condensation zone 3, represented in the figure as a horizontal submerged condenser, and is partially condensed to a carbamate solution in this zone. Via 26, a dilute carbamate solution, obtained in scrubbing ammonia and carbon dioxide out of the inert gases discharged from synthesis zone 1 via 28, is supplied to first condensation zone 3. The heat evolved during formation of this dilute carbamate solution is utilized for pre-heating of the liquid ammonia supplied via 27. To this end, a heat exchanger 19 can be installed, in which the heat released in scrubbing zone 5 can be transferred via circuit 20. The residence time in first condensation zone 3 of the reaction mixture is chosen such that in this zone also at least 30% of the equilibrium amount of urea that can be formed under the conditions prevailing, for instance 20 wt. %, is formed from carbamate. The heat released in first condensation zone 3 can be used for decomposition of further amounts of carbamate still present in the stripped urea synthesis solution. To this end, the solution discharged from stripping zone 2 via 24 is expanded to a pressure of 12–30 bar, for instance 29.5 bar, by means of expansion valve 17, and the mixture formed is introduced into gas-liquid separator 6. The liquid phase thus formed, mainly an aqueous urea solution containing also biuret, ammonia and carbon dioxide, is discharged via 25 and the gas phase, a mixture containing mainly ammonia, carbon dioxide and water vapour, via 34. The liquid phase discharged from gas-liquid separator 6 via 25 is subsequently passed, via expansion valve 17a, in heat exchange with the carbamate solution being formed in first condensation zone 3, the pressure being equal to or lower than the pressure at which expansion took place, so that further amounts of carbamate present in the expanded stripped urea synthesis solution are decomposed into ammonia and carbon dioxide. It is also possible to discharge the heat released in first condensation zone 3 by means of other process streams or water, which is thereby converted into low-pressure steam. Via 29, the non-condensed portion of the gas mixture supplied to first condensation zone 3, and via 30 the carbamate solution formed in this zone, are discharged from first condensation zone 3 and passed into second high-pressure condensation zone 4. In this zone, further condensation to carbamate solution of the gas mixture supplied via 29 takes place. The heat released thereby is discharged by means of water, which is thereby converted into low-pressure steam of 4–9 bar. The carbamate solution obtained in this second high-pressure carbamate condensation zone 4 and the noncondensed portion, if any, of the supplied gas mixture containing ammonia, carbon dioxide and water vapour are passed into synthesis zone 1 via 31.

The gas-liquid mixture that is obtained in the heat exchange in first high-pressure condensation zone 3 and discharged via 32 is passed into gas-liquid separator 7, from which the gas phase formed, a gas mixture containing ammonia, carbon dioxide and water vapour, is discharged via 36 and the liquid phase formed, a carbamate-containing urea solution, via 33. In the embodiment represented in the figure, the liquid phase obtained via 33 is contacted in contact zone 8 with the gas phase discharged from gas-liquid separator 6 via 34, the ammonia excess present in the liquid phase being expelled by the gas mixture rich in carbon dioxide, so that via 35 a liquid phase is obtained from the contact zone that is relatively less rich in ammonia. The urea-containing urea solution discharged from contact zone 8, which still contains carbamate, is passed to gas-liquid separator 9 via 35 and expansion valve 18, in which the pressure of the solution is reduced to 1–10 bar, for instance 5 bar. Via 40, a urea-containing solution is discharged from this separator. Carbamate still present in said solution is decomposed in heat exchanger 10, which is heated by low-pressure steam, following which the urea solution is fed via 41 and expansion valve 18a to heating zone 12 of the first concentration stage. Heating zone 12 may, for instance, be designed as a vertical shell and tube or heat exchanger. The urea solution to be concentrated is then led through the tubes.

The gas phase obtained in gas-liquid separator 9, a gas mixture containing ammonia, carbon dioxide and water vapour, is combined with the gas mixture containing ammonia, carbon dioxide and water vapour obtained in heat exchanger 10 and discharged via 42, upon which the combined gas mixtures, with $NH_3/CO_2$ molar ratios of between 2.0 and 4.5, for instance 4.1, are passed via 43 to low-pressure condensation zone 11 and condensed in this zone with an aqueous solution supplied via 44, for instance process condensate. The carbamate solution obtained in low-pressure condensation zone 11 is passed into the shell side of heating zone 12 via 45. Via 38, in addition, the gas mixture containing ammonia, carbon dioxide and water vapour that is obtained by combining of streams 36 and 37 is supplied to this shell side. In 12 the condensing gas mixtures flow countercurrent to the urea solution to be evaporated.

During condensation of the gas mixture supplied via 38 by means of the carbamate solution supplied via 45, enough heat is released to satisfy the heat requirements of the first concentration stage, in which the urea solution supplied via 41, which contains 70–75 wt. % urea, is concentrated to a urea content of 85–95 wt. %. The carbamate solution formed on condensation of the gas mixture in the shell side of the heat exchanger of first concentration stage 12 is discharged via 46, brought up to the synthesis pressure by means of carbamate pump 16 and passed via 47 in scrubbing zone 5. The water vapour of the mixture of concentrated urea solution and water vapour discharged from the first concentration stage via 48 is separated in water vapour separator 14 via 49, the concentrated urea solution is passed via 50 to the heating zone of the second concentration stage 13. The mixture of virtually water-free urea melt and water vapour formed here is passed via 51 to water vapour separator 15, from which the water vapour is discharged via 52 and the virtually water-free urea melt via 53.

EXAMPLE

Using the process described, urea is prepared according to the embodiment as represented in the figure in a plant with three decomposition stages with a production capacity of 1000 tonnes a day. The amounts are given in kg an hour. The pressure applied in the high-pressure part of the plant is 139 bar, after expansion in expansion valve 17 29.5 bar, in the second decomposition stage after expansion valve 17a 18.5 bar and in the last decomposition stage 5 bar. To high-pressure condensation zone 3, 23,611 kg $NH_3$ of 40° C.is supplied and 3 1,402 kg of a carbamate solution having a temperature of 117° C.and containing 13,598 kg $CO_2$, 11,727 kg $NH_3$ and 6,077 kg $H_2O$. The temperature in reaction zone 1 is 183° C.and the $NH_3/CO_2$ molar ratio 3.2. To stripping zone 2, 118,548 kg urea synthesis solution is supplied, which solution is stripped with 30,556 kg $CO_2$ while heat is being supplied. Via 24, a solution is discharged from the stripping zone that contains 41,876 kg urea, 13,445 kg $CO_2$, 11,608 kg $NH_3$ and 18,640 kg $H_2O$, and via 23 a gas mixture consisting of 36,005 kg $CO_2$, 25,990 kg $NH_3$ and 1,540 kg $H_2O$. Subsequently, the pressure of the stripped urea synthesis solution is reduced to 29.5 bar. As a result, in gas-liquid separator 6 4,444 kg is obtained of a gas mixture containing 3,561 kg $CO_2$, 730 kg $NH_3$ and 153 kg $H_2O$, which is discharged via 34. In addition, there remains 81,124 kg of a liquid phase containing 41,876 kg urea, 9,883 kg $CO_2$, 10,878 kg $NH_3$ and 18,487 kg $H_2O$.

The gas mixture discharged from the stripping zone via 23 is in part condensed in first high-pressure condensation zone 3, yielding 79,713 kg of a carbamate solution. The residence time of the mixture in this zone is chosen such that also 15,943 kg urea is formed in this solution and the solution furthermore contains 23,194 kg $CO_2$, 28,980 kg $NH_3$ and 11,596 kg $H_2O$. A further portion of the non-condensed gas mixture discharged via 29 is condensed in second high-pressure condensation zone 4, so that a solution containing 33,752 kg $CO_2$, 41,419 kg $NH_3$, 12,250 kg $H_2O$ and 15,943 kg urea, and a gas mixture containing 6,600 kg $CO_2$, 15,222 kg $NH_3$ and 451 kg $H_2O$, are supplied to synthesis zone 1.

In first high-pressure condensation zone 3, the heat released is discharged by means of liquid stream 25, on which further decomposition into $NH_3$ and $CO_2$ of the carbamate present in this flow takes place. After the reaction mixture so obtained has been subjected to a gas-liquid separation, at a pressure of 18.5 bar and a temperature of 155° C.via 36 a gas stream is obtained which consists of 7,559 kg $CO_2$, 5,374 kg $NH_3$ and 1,472 kg $H_2O$ and via 33 a solution which, besides 41,667 kg urea, contains 2,478 kg $CO_2$, 5,622 kg $NH_3$ and 16,952 kg $H_2O$. In contact zone 8 the solution is brought into countercurrent contact with the gas stream discharged via 34. Through this contact, via 37 a gas stream is obtained that contains 3,006 kg $CO_2$, 1,536 kg $NH_3$ and 470 kg $H_2O$ and has a temperature of 154° C., and via 35 a solution containing, besides 41,667 kg urea, 3,033 kg $CO_2$, 4,816 kg $NH_3$ and 16,634 kg $H_2O$.

This urea-containing solution is processed further at a pressure of 5 bar for decomposition of carbamate still present in the solution. Via 43, this yields a gas mixture containing 2,368 kg $CO_2$, 2,781 kg $NH_3$ and 1,289 kg $H_2O$. For condensation of this gas mixture, 5,546 kg process condensate containing 665 kg $CO_2$ and 2,035 kg $NH_3$, is supplied via 44. The urea solution obtained in 10, which consists of 41,667 kg urea, 665 kg $CO_2$, 2,035 kg $NH_3$ and 15,345 kg $H_2O$ and has a temperature of 130° C., is passed via 41 and expansion valve 18a to heating zone 12 of the first evaporation stage. During expansion in expansion valve 18a the temperature drops to 75° C. The heat required for concentrating is obtained by condensation in the shell side of heating zone 12 of the combined gas streams 36 and 37 countercurrently to the urea solution, use being made of the carbamate solution obtained in the low-pressure stage and supplied via 45, which contains 3,033 kg $CO_2$, 4,816 kg $NH_3$ and 4,134 kg water and has a temperature of 50° C. From heating zone 12, a gas-liquid mixture is discharged to gas-liquid separator 14, from which, at a pressure of 0.38 bar and a temperatur of 130° C., via 50 43,872 kg urea solution in water is obtained, which contains 41,667 kg urea, 2,194 kg $H_2O$ and 12 kg $NH_3$.

Per tonne of urea produced, 437 kg saturated steam of 19.6 bar and 211° C.is supplied to stripping zone 2. In second high-pressure condensation zone 4, 445 kg low-pressure steam of 5 bar is produced per tonne of urea. Of this amount, 82 kg is used in heat exchanger 10 and 63 kg in heating zone 13 of the second concentration stage. The remainder is used for maintaining, by means of steam ejectors, of the required vacuum in water vapour separators 14 and 15 and in the wastewater purification plant (not shown).

We claim:

1. In a process for the preparation of urea from the reaction of ammonia and carbon dioxide at an $NH_3/CO_2$ molar ratio of up to about 4:1 in a high pressure synthesis zone maintained at a temperature of at least about 175° C.and a synthesis pressure of between about 125 and 350 bar, to form a first urea solution containing unconverted ammonium carbamate and excess ammonia, wherein in a first decomposition stage, a portion of the uncoverted ammonium carbamate present in said first urea solution is decomposed to ammonia and carbon dioxide at a pressure of at most the pressure in said urea synthesis zone by the simultaneous supply of heat and countercurrent contact with a stripping gas, and separately removing therefrom a first gas mixture containing ammonia, carbon dioxide and water vapor, and a second urea solution still containing residual ammonium carbamate, in a first condensation stage, said first gas mixture is at least in part condensed to form a first condensate which, together with any remaining noncondensed gas mixture, is returned to the synthesis zone, in a second decomposition stage, maintained at a pressure of between about 12 and 30 bar, the second urea solution is heated by heat exchange with the condensing first gas mixture in said first condensation stage, thereby decomposing a further portion of said ammonium carbamate, and a second gas mixture thus obtained is separated from a third urea solution, in further processing stages, urea solution is subjected to at least one further decomposition step for the decomposition of ammonium carbamate and separation of ammonia and carbon dioxide thus formed, whereafter the remaining urea-containing solution is concentrated to product urea by evaporation of water in a concentration stage, the improvement essentially comprising expanding said second urea solution, to a pressure at least as high as the pressure in said second decomposition stage, and separating out a third gas mixture thereby formed prior to introduction of said second urea solution into said second decomposition stage, introducing said third gas mixture into a contact zone wherein said third gas mixture is brought into direct gas-liquid contact with said third urea solution, separately removing from said contact zone a fourth gas mixture having an $NH_3/CO_2$ molar ratio higher than said third gas mixture, and a fourth urea solution having an $NH_3/CO_2$ molar ratio lower than said third urea solution, and condensing said fourth gas mixture and returning the condensate thus formed to said high pressure synthesis zone.

2. The process of claim 1 wherein the said remaining urea-containing solution is concentrated by evaporation in said concentration stage at a temperature of 75°–130° C., and heat for said evaporation is provided by indirect heat exchange with the condensation of the fourth gas mixture from said contact stage at a temperature of 145°–110° C.

3. The process of claim 1 wherein said second gas mixture is condensed together with said fourth gas mixture.

4. The process of claim 2 wherein said second gas mixture is condensed together with said fourth gas mixture.

* * * * *